US010918871B2

(12) United States Patent
Ram Rakhyani et al.

(10) Patent No.: US 10,918,871 B2
(45) Date of Patent: Feb. 16, 2021

(54) SYSTEMS AND METHODS FOR PERIPHERAL NERVOUS STIMULATION FOR METABOLIC AND ENDOCRINE FUNCTION

(71) Applicant: Verily Life Sciences LLC, Mountain View, CA (US)

(72) Inventors: Anil Kumar Ram Rakhyani, Mountain View, CA (US); Peng Cong, Cupertino, CA (US); Stephen O'Driscoll, San Francisco, CA (US); Sean Korhummel, San Carlos, CA (US); Travis Deyle, San Jose, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 15/438,976

(22) Filed: Feb. 22, 2017

(65) Prior Publication Data

US 2017/0239484 A1 Aug. 24, 2017

Related U.S. Application Data

(60) Provisional application No. 62/306,268, filed on Mar. 10, 2016, provisional application No. 62/298,661, filed on Feb. 23, 2016.

(51) Int. Cl.
*A61N 1/00* (2006.01)
*A61N 1/372* (2006.01)
(Continued)

(52) U.S. Cl.
CPC ....... *A61N 1/37205* (2013.01); *A61N 1/3606* (2013.01); *A61N 1/36007* (2013.01);
(Continued)

(58) Field of Classification Search
CPC ............ A61N 1/37205; A61N 1/36007; A61N 1/0551; A61N 1/0556; A61N 1/37217;
(Continued)

(56) References Cited

U.S. PATENT DOCUMENTS 5,231,988 A 8/1993 Wernicke et al.
6,832,114 B1 * 12/2004 Whitehurst ............ A61N 1/326
607/40

(Continued)

FOREIGN PATENT DOCUMENTS

JP 2007503907 3/2007
JP 2013542838 11/2013

OTHER PUBLICATIONS

International Application No. PCT/US2017/019106 , "International Search Report and Written Opinion", May 11, 2017, 17 pages.

(Continued)

*Primary Examiner* — Scott M. Getzow
(74) *Attorney, Agent, or Firm* — Kilpatrick Townsend & Stockton LLP (57) ABSTRACT

Systems and methods are provided for neuro stimulation. In one implementation, a system is provided that includes a stimulator introduced into tissue at a target location and a central controller that communicates wirelessly with the stimulator. The stimulator includes a power system that receives wireless energy transmission, and an electrode system that transmits an electrical pulse for stimulating the target location. The central controller includes a power system that wirelessly delivers power to the stimulator, a communication system that wirelessly communicates with the stimulator, and a processing system that controls the power system and the communication system. The central controller may instruct the stimulator to transmit one or more electrical pulses to the target location to affect an (Continued)

endocrine function (e.g., affect the glucose level of a patient).

31 Claims, 6 Drawing Sheets

(51) Int. Cl.
  *A61N 1/36* (2006.01)
  *A61N 1/378* (2006.01)
  *A61B 5/00* (2006.01)
  *A61B 5/04* (2006.01)
  *A61B 5/145* (2006.01)
  *A61N 1/05* (2006.01)

(52) U.S. Cl.
  CPC ........ *A61N 1/36139* (2013.01); *A61N 1/3787* (2013.01); *A61N 1/37217* (2013.01); *A61B 5/04001* (2013.01); *A61B 5/14532* (2013.01); *A61B 5/425* (2013.01); *A61B 5/4227* (2013.01); *A61B 5/4244* (2013.01); *A61B 5/4255* (2013.01); *A61N 1/0551* (2013.01); *A61N 1/0556* (2013.01); *A61N 1/37223* (2013.01); *A61N 1/37288* (2013.01)

(58) Field of Classification Search
  CPC .............. A61N 1/3606; A61N 1/36139; A61N 1/3787; A61N 1/37288; A61N 1/37223; A61N 1/36185; A61N 1/36182; A61B 5/14532; A61B 5/4227; A61B 5/4244; A61B 5/425; A61B 5/4255
  See application file for complete search history.

(56) References Cited

U.S. PATENT DOCUMENTS

| | | | |
|---|---|---|---|
| 7,167,751 | B1 | 1/2007 | Whitehurst et al. |
| 7,727,147 | B1* | 6/2010 | Osorio ............... A61B 5/14528 600/345 |
| 2007/0156179 | A1 | 7/2007 | S.E. et al. |
| 2008/0051851 | A1* | 2/2008 | Lin ........................ A61N 1/05 607/42 |
| 2009/0131993 | A1 | 5/2009 | Rousso et al. |
| 2010/0069992 | A1* | 3/2010 | Aghassian ......... A61N 1/37229 607/32 |
| 2012/0130398 | A1 | 5/2012 | Ackermann et al. |
| 2013/0006324 | A1* | 1/2013 | Bradley ............... A61B 5/0538 607/45 |
| 2013/0006326 | A1 | 1/2013 | Ackermann et al. |
| 2014/0052214 | A1* | 2/2014 | Rezai .................... A61B 5/411 607/45 |
| 2014/0163639 | A1* | 6/2014 | Zhu .................... A61N 1/36139 607/46 |
| 2015/0148860 | A1* | 5/2015 | Lima ................... A61N 1/3611 607/42 |

OTHER PUBLICATIONS

Japanese Application No. 2018-541310, Office Action, dated Oct. 30, 2020, 14 pages.

* cited by examiner

SYSTEMS AND METHODS FOR PERIPHERAL NERVOUS STIMULATION FOR METABOLIC AND ENDOCRINE FUNCTION

CROSS-REFERENCE TO RELATED APPLICATIONS

The present application is related to and claims the benefit of priority of U.S. Provisional Application No. 62/298,661, filed on Feb. 23, 2016, entitled "SYSTEMS AND METHODS FOR PERIPHERAL NERVOUS STIMULATION FOR METABOLIC MODULATION") and U.S. Provisional Application No. 62/306,268, Filed on Mar. 10, 2016, entitled "SYSTEMS AND METHODS FOR PERIPHERAL NERVOUS STIMULATION FOR METABOLIC MODULATION, the full disclosure of each is incorporated herein in its entirety.

BACKGROUND

Technical Field

The present disclosure relates generally to the fields of metabolic disorder treatment and neuro stimulation. More particularly, and without limitation, the present disclosure relates to systems and methods for the management of metabolic disorders using an implanted neural stimulator.

Background Description

Metabolic disorders, including pre-diabetic and diabetic conditions, cause the incorrect production of chemical signals and/or inappropriate response of downstream organs to those signals, either in terms of timing or magnitude, which in turn lead to associated health problems. This incorrect chemical signaling often causes downstream organs to have to work harder than expected and then those organs become overstressed and less responsive to the chemical signals, which accelerates the degradation. In the case of diabetes, these chemical signals are insulin and glucagon. Often the production of these signals is promoted or inhibited by electrical signals from the nervous system (most commonly the autonomic nervous system).

Existing treatments involve medically managing chemical imbalances by introducing these chemical signals, or close matches thereof, from outside the body (e.g. insulin pen injections, insulin pumps). These treatments commonly use synthetic versions of those chemicals (insulin or glucagon) or employ drugs which treat the condition. However, these treatments can have very significant unintended consequences to health, and have ongoing negative impacts on comfort and lifestyle.

The nervous system of a human has two main parts: the central nervous system (i.e., the brain and spinal cord); and the peripheral nervous system (i.e., the nerves that carry pulses to and from the central nervous system). The nervous system controls voluntary and involuntary actions of different body parts (e.g., muscles, limbs, organs, etc.) by transmitting and receiving signals to and from the different parts of the body. When a portion of a vertebrate's nervous system becomes damaged (e.g., by disease or injury) the voluntary or involuntary function of a person's body parts, organs, or metabolic systems may be restricted or a person may experience partial or total paralysis or dysfunction. For those who have suffered nervous system damage, efforts have been devoted to using implanted electrode arrays to sense nerve signals and to stimulate nerves in an attempt to restore function to the effected body parts or organs. Although these efforts in some case have produced some positive results, there is much room for significant advancement in the technology in order to render it functional and viable as a long term solution. For example, the large size of known wired electrodes and arrays, and the wires connecting them to a central controller, limit both the functionality and the suitability of these approaches to many applications.

SUMMARY

In one aspect, the present disclosure is directed to one or more implanted neural stimulators to provide electrical stimulation to the nervous system innervation pathways which can promote or inhibit the production and secretion of appropriate chemical signals. In an illustrative embodiment, the chemical signals include insulin and glucagon for the treatment of diabetes mellitus.

In another aspect, the present disclosure is directed to a system for neuro stimulation. The system may include a micro particle or other neural stimulator that is introduced into tissue at a target location and a central controller that communicates wirelessly with the micro particle. The micro particle may include a power system that receives wireless energy transmission and an electrode system that transmits an electrical pulse for stimulating the target location. The micro particle may also include a processing system that controls the power system and the electrode system. The central controller may include a power system that wirelessly delivers power to the micro particle and a communication system that wirelessly communicates with the micro particle. The central controller may also include a processing system that controls the power system and the communication system. The central controller may instruct the micro particle to transmit one or more electrical pulses to the target location to stimulate a function of a patient's endocrine system which can modulate aspects of the patient's metabolic system.

The system may include a multicontact cuff or microelectrode array or other suitable neural stimulator for targeted stimulation. The electrode array can be powered wirelessly from outside the body or through wires from an implanted battery operated pulse generator.

In another aspect, the present disclosure is directed to a method of stimulating a function of the endocrine system. The method may control the stimulation using a closed-loop feedback of blood or correlated body glucose levels.

In another aspect, the present disclosure is directed to a method of controlling insulin production in a time interval prior to an anticipated patient meal.

BRIEF DESCRIPTION OF DRAWINGS

The accompanying drawings, which are incorporated in and constitute part of this specification, and together with the description, illustrate and serve to explain the principles of various exemplary embodiments.

DETAILED DESCRIPTION

Figure 1:
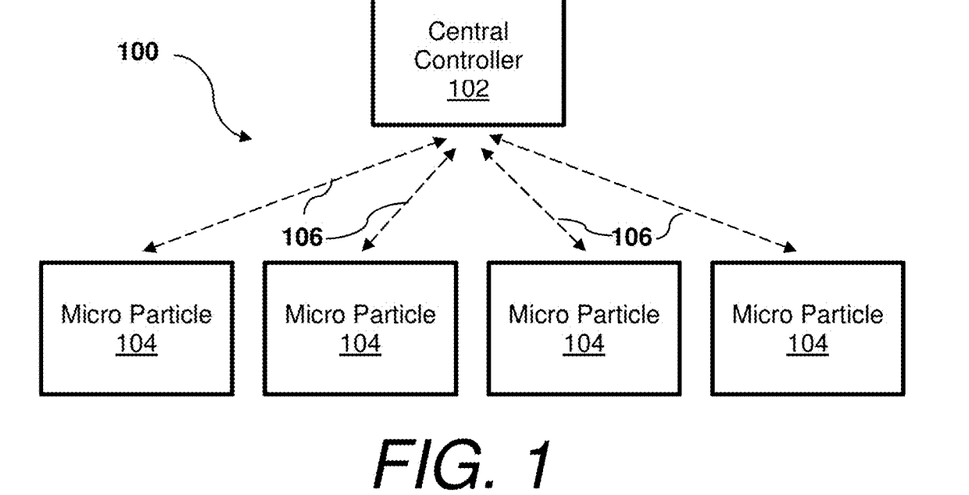
FIG. 1 is a schematic of a neuro stimulation system, according to an exemplary embodiment

FIG. 1 shows a schematic diagram of a coordinated neuron stimulation system 100, according to an exemplary embodiment. System 100 may include a central reader/controller, which will be referred to herein as a central controller 102. System 100 may also include one or more micro particles 104 configured to communicate with central controller 102. System 100 may be configured such that central controller 102 powers the micro particles 104 via wireless energy transmission. System 100 may be configured to wirelessly communicate with the micro particles 104, via wireless data links 106, without the use of leads as typically used for electrode stimulators. Central controller 102 and the micro particles 104 may send and receive informational signals back and forth, which may include, for example, data, instructions, protocols, configurations, and the like. When the term information or informational signal(s) is used herein this may refer to one or more of the categories of information listed above.

In some embodiments, system 100 may include a single central controller 102 and a single micro particle 104. In some embodiments, system 100 may include a single central controller 102 and a plurality of micro particles 104. For example, in some embodiments, the number of micro particles 104 that system 100 includes may be 2 to 5, 6 to 10, 11 to 15, 16 to 20, 21 to 50, 51 to 100, 101 to 1000, or more micro particles (uPs) ranging 2 to 100 or more. In some embodiments, system 100 may include multiple central controllers 102 and multiple micro particles 104. The number of central controllers 102 and multiple micro particles 104 may be determined and/or adjusted based on a number of variables, including for example, the body part that is to be stimulated, the function of the body part to be stimulated, the distance between the micro particles 104, the extent of damage to the person nervous system, and the size and power of central controller 102. Although the following description is primarily directed to an embodiment of system 100 having more than one micro particle 104, the description is equally applicable to an embodiment of system 100 having just one micro particle 104, besides the description related to coordination of multiple micro particles 104.

Figure 2:
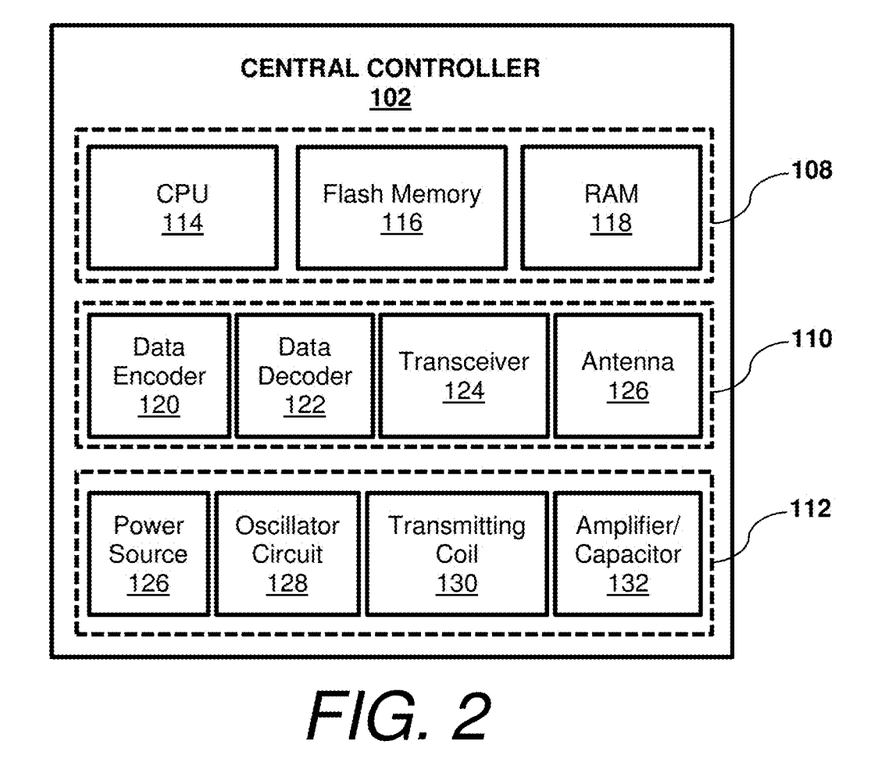
FIG. 2 is a schematic illustration of a central controller, according to an exemplary embodiment.

FIG. 2 shows a schematic of central controller 102, according to an exemplary embodiment. Central controller 102 may include a processing system 108, a communication system 110, and a power system 112. Processing system 108 may be configured and responsible for controlling the overall operation of central controller 102 and coordinating the operation of the micro particles 104. Communication system 110 may be configured to wirelessly send informational signals to the micro particles 104 and receive informational signals from the micro particles 104. The power system 112 may be configured to power the central controller 102 and power the micro particles 104 using wireless energy transmission.

In some embodiments, central controller 102 may include additional components depending on desired functionality and/or the needs of the implementation. By way of example, additional components include data ports, disk drives, a user interface, speaker(s), computer network interface(s), indicator light(s), and/or display. In some illustrative embodiments, the controller may be an intelligent signal processor which can have secured data link with the other devices over the wireless network. In some illustrative embodiments, the controller may provide power to the micro particles through electromagnetics, acoustic, or optical waves. The configuration of central controller 102 may be also be adjustable using any combination of hardware and software components.

Processing system 108 of central controller 102 may include one or more processors, including for example, a central processing unit (CPU) 114. The CPU 114 may include any suitable type of commercially available processor or may be a custom design. Processing system 108 may include additional components, for example, non-volatile memory (e.g., a flash memory 116), volatile memory (e.g., a random access memory 118 (RAM)), and other like components, configured to store information (e.g., data, program instructions, protocols, configurations, and the like) to enable the control and overall operation of central controller 102 and the micro particles 104.

Communication system 110 may utilize a variety of wireless data transmission methods for communicating back and forth with the micro particles 104 via one or more wireless data links 106 (see FIG. 1). For example, in some embodiments, communication system 110 may utilize radio data transmission, Bluetooth, near field communication (NFC), infrared data transmission, electromagnetic induction transmission, and/or other suitable transmission methods. Data link may be based on the electromagnetic (radio data transmission, Bluetooth, near field communication (NFC), electromagnetic induction transmission), acoustic or optical (infrared data transmission) based.

According to an exemplary embodiment, as shown in FIG. 2, communication system 110 of central controller 102 may utilize radio data transmission and include a number of components to support such transmission, such as a data encoder 120, a data decoder 122, a transmitter and a receiver or a transceiver 124, and/or an antenna 125. In some embodiments of communication system 110 may include two antennas, for example, one receiver antenna and one transmitter antenna. Also, in some embodiments, communication system 110 may be configured to transmit and receive data using a plurality of different wireless transmission methods.

Communication system 110 may be configured to establish data links between central controller 102 and the micro particles 104. Communication system 110 may be configured to transmit informational signals to the micro particles 104 while simultaneously receiving informational signals from the same or other micro particles 104. Processing system 108 may initiate the transmission of one or more informational signals to one or more of the micro particles 104 by conveying a message to the data encoder 120, which may then provide an encoded message to be transmitted through the antenna 125 via the transceiver 124. Processing system 108 may receive transmitted informational signals from the micro particles 104 when a transmission is received by the antenna 125 via the transceiver 124, which in some embodiments, may be decoded by the data decoder 122. Each micro particle 104 may be uniquely addressed, which may enable central controller 102 to individually communication with each micro particle 104. Unique addressing of the micro particles 104 is described in more detail below. In some embodiments, data may be transmitted without encoding or decoding the data by communication system 110.

Further, in some embodiments, recognition, pairing, or other signaling techniques may be used in place of addressing for transmitting data to and from micro particles 104.

Power system 112 may be configured to use wireless energy transmission to power the micro particles 104. In some embodiments, power system 112 may utilize, for example, inductive coupling, resonant inductive coupling, radio frequency, or the like to wirelessly transmit power.

According to an exemplary embodiment, as shown in FIG. 2, power system 112 may utilize resonant inductive coupling and may include a power source 126, an oscillator circuit 128, and/or a transmitting coil 130. Power source 126 may provide any suitable source of power, such as an AC source or a DC source. In some embodiments, the power source 126 may be, for example, a battery, a capacitor, a photovoltaic array, or the like. Oscillator circuit 128 may be powered by the power source 126 and drive the transmitting coil 130. In some embodiments, the signal from the oscillator circuit 128 may be amplified by a power amplifier 132 which may be coupled through, for example, a capacitor, to the transmitting coil 130. The transmitting coil 130 may be mutually coupled with the receiving coils on the micro particles 104, which will be discussed in more detail below. The coupled coils may transfer electromagnetic energy from the transmitting coil 130 through the body tissue to the receiving coils of the implanted micro particles 104 by way of mutual induction.

Figure 3:
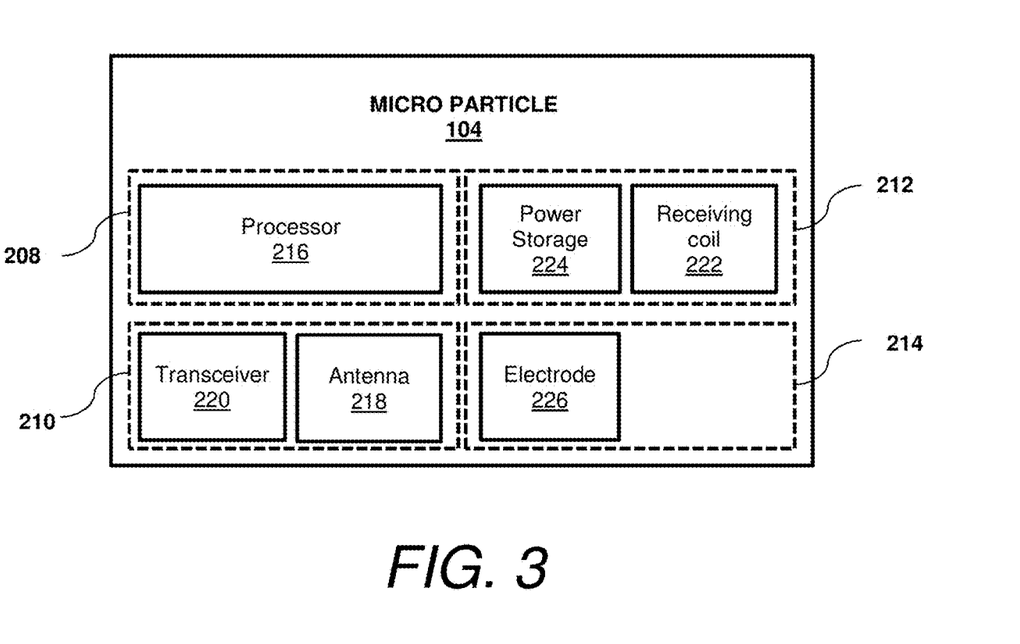
FIG. 3 is a schematic illustration of a micro particle, according to an exemplary embodiment.

FIG. 3 shows a schematic diagram of an individual micro particle 104, according to an exemplary embodiment. Micro particle 104 may include a processing system 208, a communication system 210, a power system 212, and an electrode system 214. Processing system 208 may control the overall operation of the micro particle 104. Communication system 210 may communicate with central controller 102 by sending and receiving informational signals. The power system 212 may power the processing system 208, the communication system 210, and the electrode system 214 of the micro particle 104. The electrode system 214 may be controlled via the processing system 208 based on informational signals received from the central controller 102.

Processing system 208 may include a processor 216 configured to process, for example, data, instructions, protocols, configurations, and the like. For example, the processor 216 may receive informational signals containing instructions from the central controller 102 and based on the instructions control the operation of the electrode system 214 (e.g., stimulate nerve or sense nerve pulses).

Communication system 210 may utilize the same wireless data transmission method utilized by communication system 110 of the central controller 102. Communication system 210 may include an antenna 218 and a transceiver 220 to establish wireless communication with central controller 102. In order to minimize the number of components and size of the micro particles 104, antenna 218 and transceiver 220 may both be dual function, for example, each may receive and transmit signals. In some embodiments, communication system 210 may include a separate transmitter and a separate receiver rather than the dual function transceiver 220. Similarly, in some embodiments, communication system 210 may include a separate transmitter antenna and a separate receiver antenna rather than the dual function antenna 218. Although not shown, in some embodiments, communication system 210 may include an encoder and decoder. The encoder and/or decoder may be digital enabling better handling of signal attenuation. In some embodiments, all coding and decoding of the informational signals may be done by the central controller 102.

The power system 212 for micro particle 104, like the power system 112 for central controller 102 may use wireless energy transmission, including, for example, inductive coupling, resonant inductive coupling, radio frequency (RF) link, or the like to wirelessly transmit energy. Power system 212 may utilize the same wireless energy transmission method as power system 112 of central controller 102.

According to an exemplary embodiment, as shown in FIG. 3, power system 212 may utilize resonant indicative coupling. Power system 212 may include a receiving coil 222 that may be mutually inductively coupled to the transmitting coil 130 of central controller 102. In some embodiments, power system 212 may also include a power storage device 224 (e.g., battery, capacitor, or a power cell). The processing system 208, communication system 210, and the electrode system 214 may be powered by the energy received via the receiving coil 222. In some embodiments, power system 212 may also include a ground. Embodiments of power system 212 utilizing an RF link for transmission of power may utilize a different type of antenna, thus eliminating the need for receiving coil 222.

The electrode system 214 may include a single electrode 226 or multiple electrodes. In some embodiments the electrode 226 may function as a cathode (i.e., negative electrode), an anode (i.e., positive electrode), or both (i.e., switch between). Embodiments where the electrode system 214 includes multiple electrodes 226, one electrode may function as a cathode and another electrode may function as an anode. The electrode 226 may function as either a stimulating electrode by transmitting electrical pulses that excite nerves by inducing a flow of ions through the nerve cell membrane or may function as a sensing electrode by detecting electrical pulses transmitted along the neuron structure (e.g., axon, axon terminal, dendrites, etc.). The electrode 226 may function as either a stimulating electrode by electrical pulses that excite nerves by inducing a flow of ions through the nerve cell membrane or may function as a sensing electrode by detecting electrical pulses transmitted along the neuron structure (e.g., axon, axon terminal, dendrites, etc.). Stimulation is an input current or voltage pulse. Reaction is an action potential generation.

The one or more electrodes 226 of electrode system 214 may be positioned at one or more locations about the micro particles 104. For example, for a cube shaped micro particle 104, electrode 226 may be position on one side and one or more electrodes may be position on the other sides. For a spherical shaped micro particle 104, one or more electrodes 226 may extend, for example along a portion of the outer surface or in some embodiments the electrode may extend the full circumference around the sphere (e.g., ring shaped electrode).

In some embodiments, the orientation and direction electrode 226 is facing may be identifiable on the micro particle 104 and thus the electrode may be oriented during placement such that the electrode touches or faces a target location. In some embodiments, with more than one electrode, after placement of the micro particle 104 the active electrode may be advantageously selectable. For example, the electrode best oriented to stimulate a target location may be selected as the stimulating electrode.

In some embodiments, the orientation of the electrode 226 relative to a target location may be randomly determined based on the orientation of the micro particle 104 upon placement. For example, some micro particles 104 may be positioned such that the electrode 226 is facing a target location while others may be positioned such that the electrode 226 is not generally facing a target location. In some embodiments, the micro particle 104 may adjust the power of the electrical pulse based on the positioning of the electrode 226 relative to the target location. For example, an electrode proximate to and facing a target location may transmit an electrical pulse at less power than an electrode a distance from and facing away from a target location. The implementation procedure is not in the scope of this disclosure, but in one exemplary embodiment, the initial phase, the controller may control the underlying uPs can be in combinations of stimulating and sensing mode. This will result in the mapping of uPs location and its proximity to the target sites. At the time of targeted stimulation, single or multiple uPs will be activated by the controller to improve selectivity in the low power mode.

The electrode system 214 may stimulate a nerve cell or portion of a nerve cell positioned proximate to the micro particle 104 by transmitting one or more electrical pulses. The electrical pulses may vary, for example, in power (e.g., voltage and/or current), amplitude, speed, duration, waveform, and frequency. The power of the electrical pulses may vary, for example, by varying either the voltage and/or current at which the pulses are transmitted. The power may vary for example from about X to about Y. The corresponding voltage may vary, for example, from about X to about Y. The corresponding current may vary, for example, from about X to about Y.

Fundamentally, with the electrode close enough, the required voltage can be as low as 10-100 mV. In some embodiments, due to close proximity of the micro particle, the achievable voltage threshold may be lower than any microelectrode or cuff electrode. The range of power by which electrode system 214 may stimulate a nerve cell is less than that of the prior art, which may reduce the risk of injury or atrophy to the nerve cell and surrounding tissue.

Each micro particle 104 may be uniquely addressed. For example, each micro particle 104 may be uniquely electromagnetically addressed. Each uPs may consists of unique identification number programmed in non-volatile memory Or as an unique part of the system such as electrical, mechanical Or fabrication or hard coded during fabrication. To address individual uP, the data communication (electromagnetic/acoustic/optical) signal may modulated with the uP address and only the uP with matched address (after decoding) respond to the activation. As a result of the unique addressing, central controller 102 may send unique informational signals to each individual micro particle 104. Similarly, central controller 102 may be able to individually identify informational signals received from each micro particle 104. In some embodiments, one or more of the micro particles 104 may have the same addressing so that the same information may be transmitted to multiple micro particles 104 at the same time.

Figure 4:
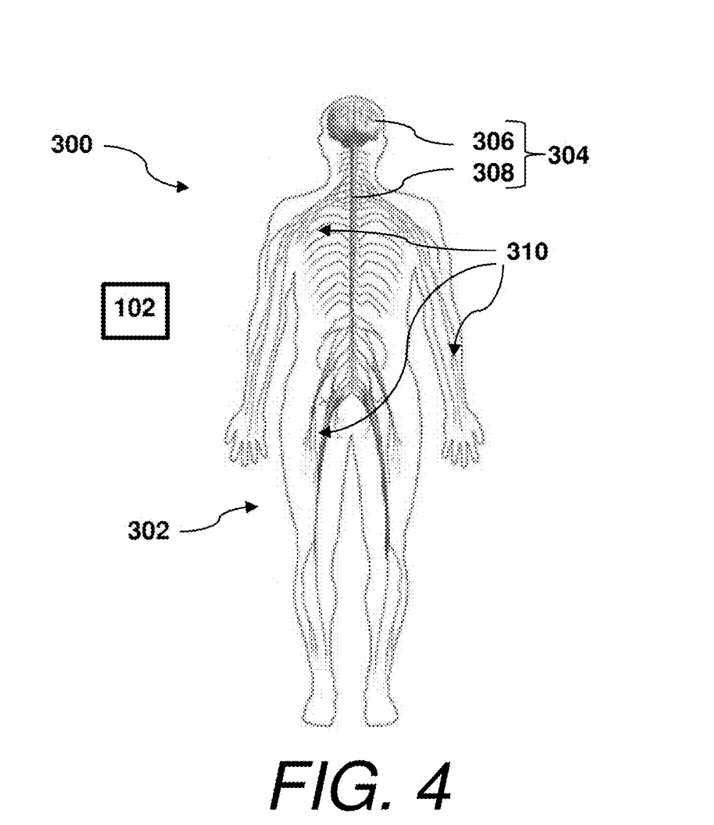
FIG. 4 is an illustration of a nervous system of a human.

FIG. 4 shows an illustration of a nervous system 300 of a human subject 302. Nervous system 300 is made up of two main parts: the central nervous system 304, which includes the brain 306 and the spinal cord 308, and the peripheral nervous system 310, which includes the nerves that go from the spinal cord to the arms, hands, legs, and feet. The peripheral nervous system 310 is made up of several nerve systems: the sensory nervous system, the motor nervous system, the somatic nervous system, and the autonomic nervous system. The sensory nervous system includes sensor nerves that send information to the central nervous system 304 from internal organs or from external stimuli. The motor nervous system includes motor nerves that carry information from the central nervous system 304 to organs, muscles, and glands. The somatic nervous system includes somatic nerves that control skeletal muscle as well as external sensory organs. The autonomic nervous system includes autonomic nerves that control involuntary muscles (e.g., cardiac muscles).

Figure 5A:
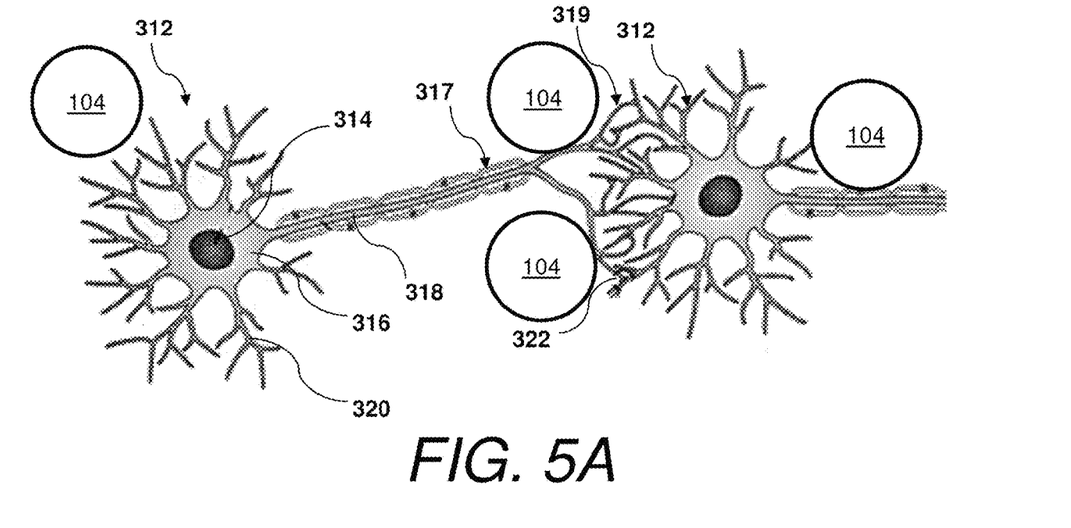
FIG. 5A is an illustration of a pair of neurons of the nervous system of FIG. 4.

The nervous system 300 is made up of billions of nerve cells, which may also be referred herein as neurons. FIG. 5A is an illustration of two interconnected nerve cells 312, which may be part of a network of interconnected nerve cells. Nerve cell 312 on the left as illustrated may be characterized as the transmitting nerve cell while nerve cell 312 on the right may be characterized as the receiving nerve cell. Each nerve cell 312, as shown in the FIG. 5A, may include among other things, a nucleus 314, a cell body 316, an axon 318, axon terminals 319 and dendrites 320. The dendrites 320 collect electrical signals while the cell body 316 and nucleus 314 integrates the incoming signals and transmits outgoing nerve signals down the axon 318 to the axon terminals 319. The axon 318 may be surrounded by a myelin sheath 317 that facilitates transmission of nerve pulses to the axon terminals 319. The axon terminals 319 may pass the outgoing signal to dendrites 320 of the receiving cell. The electrical signals may be transmitted from the transmitting cell to the receiving cell across one or more synapses 322.

Nerve signals or pulses, which may also be referred to as action potential, is a coordinated movement of sodium and potassium ions across the cell membrane. The inside of a nerve cell is slightly negatively charged, for example, the resting membrane potential is about −70 to −80 mV. A disturbance or stimulation (e.g., a mechanical, electrical, or chemical) can cause a few sodium channels in a small portion of the membrane to open and the position charge that they carry depolarizes the cell (i.e., makes the inside of the cell less negative). When the depolarization reaches a certain threshold value more sodium channels are opened enabling more sodium flow in and triggers an action potential. In other words, the inflow of sodium ions reverses the membrane potential in that area (i.e., making it positive inside and negative outside). When the electrical potential reaches about +40 mV inside, the sodium channels shut down and let no more sodium ions inside. The developing positive membrane potential causes potassium channels to open and potassium ions leave the cell through the open potassium channels. The outward movement of the positive potassium ions makes the inside of the membrane more negative, repolarizing the cell. When the membrane potential returns to the resting value the potassium channels shut down and potassium ions can no longer leave the cell. This sequence of events occurs in a local area of the nerve cell membrane, but these changes get passed on to the next area of the nerve cell membrane, then to the next area, and so down the entire length of the axon. Thus, the action nerve pulse, nerve signal, or action potential gets transmitted (i.e., propagated) down the nerve cell and transmitted to other nerve cells through synapses. A typical nerve cell may have thousands of synapses enabling it to communication with thousands of other nerve cells, muscle cells, glands, etc.

The action potential is often referred to as an "all-or-none" response because once the membrane reaches a threshold, it will depolarize to +40 mV. Action potentials may be propagated rapidly. For example, typical neurons can conduct 10 to 100 meters per second depending on the diameter of the axon (i.e., larger axon produce faster propagation). Neurons may vary in size depending on the type of neuron. For example, some neurons have an average diameter of as little as about 5 microns while others may have an average diameter of about 100 microns. Neurons can vary structure and many neurons can be anatomically characterized as unipolar, multipolar, or bipolar.

When a portion of a person's nervous system becomes damaged (e.g., by disease or injury) the voluntary or involuntary function of a person's body (e.g., limb or organ) may be restricted or a person may experience partial or total paralysis or dysfunction. System 100 may stimulate a function of a limb or an organ by sending electrical pulses to one or more nerves and in some embodiments sensing nerve pulses from one or more nerves using one or more micro particles 104. The electrical pulses transmitted from the micro particles 104 to the one or more nerves may function as the stimulation that cause the sodium channels to open depolarizing the cell and ultimately triggering a nerve pulse or action potential. The following description refers to the use of a plurality of micro particles 104; however, in some embodiments of system 100 may utilize a single micro particle 104.

Central controller 102 may be a portable or wearable device that a person may carry with them. The micro particles 104 may be implantable into the tissue of a person or animal. Implantation may be planned or more random. For example, in some embodiments the implantation may be planned such that individual micro particles 104 may be implanted at or proximate to specific nerves or portions of a nerve identified to control or transmit the nerve signals that trigger the function which the system is trying to stimulate. In other embodiments, the general region of the target nerve or nerves may be known, but the micro particles 104 may be more randomly distributed in the region of the nerve or nerves rather than being individually placed at predetermined locations. In some embodiments, as illustrated in FIG. 5A, micro particles 104 may be implanted near the dendrites 320, synapses 322, axons 318, or axon terminals 319, of one or more nerve cells 312.

The micro particles 104 may vary in size. In some embodiments, for example, the average diameter of the micro particle 104 may be about 500 microns to about 400 microns, about 400 microns to about 300 microns, about 300 microns to about 200 microns, or about 200 microns or less. Generally, the micro particles may be about the size of a grain of sand. The minimal size of the micro particles will significantly reduce the likelihood of trauma compared to the larger prior art electrodes currently utilized. For example, prior art nerve cuffs designed to wrap around a peripheral nerve can cause trauma to the target nerve as well as the surrounding nerves during installation and operation due to the large size and complexity of the installation.

The microscopic size of the micro particles 104 enables more precise and refined placement with respect to the corresponding microscopic nerve cells when compared to other electrodes that are an order of magnitude larger. For example, an electrode that is about 1 millimeter in diameter is 10 times the size of a nerve cell that has an average diameter of 100 microns. Thus, the 1 millimeter electrode covers the entire nerve cell and may even cover portions of neighboring nerve cells. In contrast, the micro particles 104 may be about the same order of magnitude of the nerve cell (e.g., 200 micron micro particle 104 and 100 micron nerve cell 312). Thus, the micro particle may be positioned more precisely in order to stimulate a specific nerve cell or portion of a nerve cell. In some embodiments, a micro particle 104 may be placed at or adjacent a specific portion of the nerve 312. For example, a micro particle may be placed at a dendrite branch or limb or may be placed along an axon 318 or at an axon terminal 319 of a nerve 312. In some embodiments, a micro particle 104 may be placed at or near a synapse 322 connecting two nerves 312. In some embodiments, the relative size of the micro particles 104 may allow placement further down the branches of the dendrites 320 or axon terminals 319. This may allow finer location targeting for stimulation and sensing of nerve pulses.

More refined placement of the micro particles 104, which advantageously enables more refined targeting for stimulation and sensing may reduce the potential for inadvertently stimulating nerve cells that were not intended, which in some cases may cause inadvertent function stimulation and other side effects. For example, stimulating the larger fibers of the vagus nerve as part of treatment for epilepsy could inadvertently stimulate too broadly causing heart arrhythmias. Signals sensed from a larger fiber are also more difficult to interpret because of the number of signals not of interest.

More refined placement of the micro particles 104 and closer proximity placement to the target nerve or portion of the nerve, in addition to reducing the likelihood for inadvertent nerve cell stimulation, also allows the strength of the electrical pulses transmitted from the micro particles 104 to be reduced. For example, the reduced size of the micro particles 104 allows for placement at closer proximity to the target portion of the nerve cell thereby enabling less power (e.g., voltage or current) to be used to stimulate the cell and trigger an action potential. Coulomb's law describes the relationship between distance and current intensity as $I=k(i/r^2)$. $I$=current required; $k$=constant; $i$=minimal current; $r$=distance from nerve. Thus, by reducing the distance from the nerve, the minimal current may be reduced. Reducing the strength of the electrical pulses may be beneficial in some situations because electrical pulses above certain power thresholds can cause atrophy to the neural structures over time. Fundamentally, with the electrode close enough, the required voltage can be as low as 10-30 mV. In some embodiments, due to close proximity of the micro particle, the achievable voltage threshold may be lower than any traditional microelectrode or cuff electrode. Stimulating the nerve cells and triggering an action potential using less power (e.g., current and/or voltage) can reduce or prevent atrophy of the neural structures proximate to the micro particles.

An illustrative system and method will be herein described with reference to the pancreas and its innervation, with the understanding that the small intestine and liver can also be implicated in metabolic disorders, and can be treated in analogous fashion as that described with reference to the pancreas.

Figure 5B:
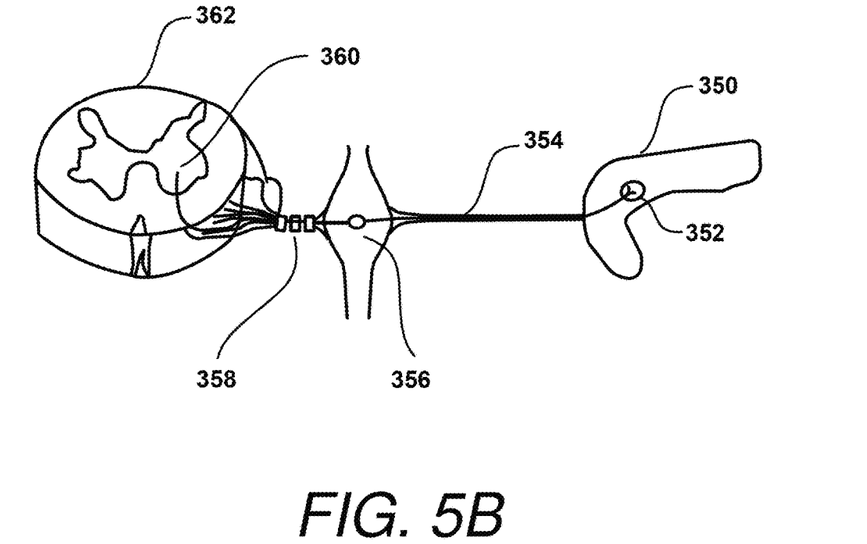
FIG. 5B is an illustration of the innervation of pancreatic islets.

The pancreatic islets are richly innervated by autonomic nerves. As depicted in FIG. 5B, the pancreas 350 contains islets 352 that include beta cells which store and release insulin, and postgangionic nerves include islet parasympathetic nerves 354, which emanate from the intrapancreatic ganglia 356, which are controlled by preganglionic vagal nerves 358. The preganglionic vagal nerves emanate from the spinal cord 360 located within the spine 362.

The islet postganglionic nerves also include sympathetic nerves with the nerve cell bodies located in ganglia outside the pancreas, similar to the parasympathetic intrapancreatic ganglion 356 depicted in FIG. 5B. The sensory nerves originate from dorsal root ganglia near the spinal cord.

Inside the islets 352, nerve terminals are proximate to the pancreatic endocrine cells. The nerve terminals contain neurotransmitters such as acetylcholine and norepinephrine, as well as several neuropeptides, including vasoactive intestinal polypeptide (VIP), pituitary adenylate cyclase-activating polypeptide (PACAP), gastrin-releasing polypeptide (GRP), and cocaine- and amphetamine-regulated transcript (CART) in parasympathetic nerves; neuropeptide Y (NPY) and galanin in the sympathetic nerves; and calcitonin gene-related polypeptide in sensory nerves. Through autonomic innervation, neuronal input to the pancreatic endocrine cells regulates hormone release. Parasympathetic input to the pancreatic beta cells stimulates insulin secretion. Parasympathetic stimulation of insulin secretion is part of a process known as cephalic phase stimulation of insulin secretion. Cephalic phase stimulation derives from sensory stimuli and neural inputs that are activated when food is first eaten. There is activation of parasympathetic preganglionic neurons 358 whose axons are in the vagus nerve. These activate the postganglionic neurons 354 that stimulate insulin secretion before any change in blood glucose occurs by eating. This is an example of feedforward regulation: insulin secretion is stimulated in anticipation of the rise in blood glucose.

Sympathetic input to the pancreatic beta cells inhibits insulin secretion. Sympathetic inhibition of insulin secretion occurs, for instance during exercise or adrenal events, where muscle cells consume glucose at higher rates. By inhibiting the production of insulin, which stimulates glucose uptake by non-muscle cells, more glucose is available for the muscle cells and physical exertion.

System 100 as described herein may be utilized in a variety of methods for treating conditions related to metabolic disorders by providing sympathetic and/or parasympathetic neuronal stimulation. Various methods of utilizing system 100 will now be explained.

Figure 6:
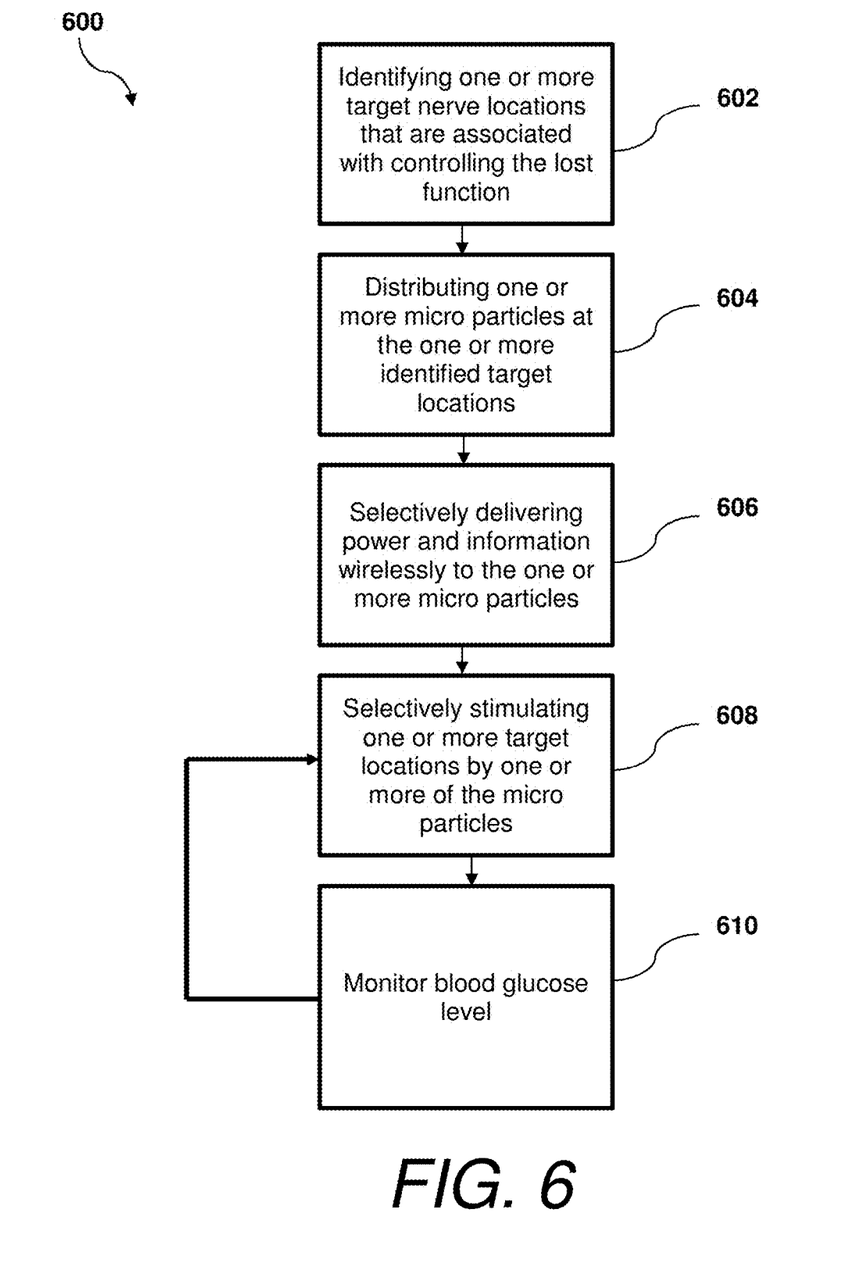
FIG. 6 is a flow chart illustrating a method of coordinated neuro stimulation, according to an exemplary embodiment.

According to an exemplary embodiment illustrated in FIG. 6, system 100 may be utilized for a method 600 of stimulating the sympathetic or parasympathetic functions of one or more organs, for instance the pancreas, of a person. Method 600 may be used for treating a person (e.g., a patient) who has diabetes, prediabetes, metabolic syndrome, or other indications that are diagnosed as related to blood sugar, such as depression, mood swings, irritability, hyperactivity, anxiety, panic attacks, mineral deficiencies, adrenal gland depletion, weight gain, hypoglycemia, candida overgrowth, hypercholesterolemia, nutrition disorders and/or chronic fatigue.

As shown in FIG. 6, method 600 may include identifying one or more target locations of one or more nerve cells that are associated with controlling the lost function, at step 602. The scope of what constitutes a target location may vary. For example, a target location may be a specific nerve cell, a specific portion of a nerve cell (e.g., dendrite, axon, axon terminal, myelin sheath, or synapse), a cluster of nerve cells, a ganglion, a nerve plexus, or a region of tissue containing one or more nerve cells. In some embodiments, target locations may be adjacent or proximate to one another, for example, two adjacent nerve cells or an axon and axon terminal of the same nerve cell. In some embodiments, target locations may be a distance apart. In some embodiments, the distance apartment may be, for example, less than, about 5 millimeters, about 10 millimeters, about 15 millimeters, about 20 millimeters, about 25 millimeters, or about 50 millimeters. In some embodiments, the distance apartment may be, for example, greater than, about 5 millimeters, about 10 millimeters, about 15 millimeters, about 20 millimeters, about 25 millimeters, or about 50 millimeters. In an illustrative embodiment, the location is proximate the celiac ganglion. In an illustrative embodiment, the location is proximate an autonomic ganglion. In a further illustrative embodiment, the location is proximate the pancreatic plexus.

Next, step 604 of method 600 may include distributing one or more micro particles into the patient (e.g., into the tissue) at the one or more identified target locations. In some embodiments, distributing the one or more micro particles 104 may include placement of one or more individual micro particles at or in the vicinity of one or more target locations. In some embodiments, distributing the one or more micro particles 104 to a target location may include directing them to a target location (e.g., a region) and within the region the one or more micro particles 104 may be more randomly distributed within the region. In some embodiments, distributing or placement of the micro particles 104 may be aided by imaging guidance. For example, a magnetic resonance (MR) imaging system may be used to provide real-time visual feedback during the distribution or placement of the micro particles.

In illustrative embodiments, the target locations can include different types of nerves, for example, motor nerves, sensory nerves, or autonomic nerves. In an illustrative embodiment, the target location is the vagus nerve.

In some embodiments, prior to distribution of the one or more micro particles, method 600 may include initiating a startup of system 100, which may include powering up of the micro particles and testing the wireless communication between central controller 102 and the micro particles 104. In some embodiments, powering up of the micro particles and testing of the wireless communication (i.e., startup) may be conducted after distribution of the one or more micro particles. In some embodiments, startup may be conducted for each micro particle after distribution of each micro particle.

Once the one or more micro particles are distributed and in position, step 606 of method 600 may include selectively delivering power and information wirelessly to one or more micro particles 104. As described herein, each individual micro particle 104 may be uniquely addressed. Thus each central controller 102 may transmit unique information to each micro particle 104.

Step 608 of method 600 may include central controller 102 selectively stimulating one or more target locations by one or more of the micro particles 104. Stimulation by the one or more micro particles 104 may trigger and action potential at the target locations, which may propagate down the nerve and on to other interconnected nerves. Central controller 102 may execute a stimulation protocol configured to conduct a coordinated stimulation by one or more of the micro particles 104 at one or more of the target locations. The stimulation protocol may be configured to stimulate (e.g., restore) a function of a limb, an organ, or other body part of a patient. The stimulations by the one or more micro particles 104 may be coordinated, for example, the stimulations may be simultaneous, the stimulations may be sequenced, or the stimulations may be patterned. In some embodiments, the stimulations may be configured to cascade, for example, central controller 102 may instruct a first micro particle 104 to stimulate a first target location and then instruct a second micro particle 104 to stimulate a second target location and then instruct a third micro particle 104 to stimulate a third target location and so on.

In some embodiments, method 400 may also include selectively sensing nerve pulses at one or more target locations by one or more of the micro particles, at step 410. Central controller 102 may select which of the micro particles 104 sense nerve pulses and which stimulate nerve pulses. In some embodiments, central controller 102 may selectively instruct one or more micro particles 104 to switch from stimulating to sensing based on a stimulation protocol. In some embodiments, a micro particle 104 may stimulate and sense, for example, by using one electrode 226 to sense and another electrode 226 to stimulate. The nerve pulses may be sensed by one or more of the micro particles 104 and informational signals indicative of the sensed nerve pulse may be transmitted back to the central controller 102.

In an exemplary embodiment, the glucose level of a patient can be monitored at step 610, and the result of this measurement used as a feedback datum for the process 600. Blood glucose level can be monitored by numerous methods, for example by an indwelling continuous blood glucose (CGM) sensor, skin patch, glucose-sensing bioimplant, non-invasive monitor or using blood test strips. Other types of glucose monitors may be utilized. In some embodiment, continuous monitoring of a glucose level of a patient is performed using at least one glucose monitor.

Steps 608 and 610 of method 600 may be repeated and in between steps the stimulation and/or sensing protocol may be adjusted in order to achieve a desired result (e.g., the desired blood- or body glucose level) acting as a feedback loop. In some embodiments, method 600 may include selectively adjusting (e.g., increasing or decreasing) the power of one or more micro particle stimulations based on the sensed nerve pulses (e.g., the timing of the sensed nerve pulses). In some embodiments, between repeating of steps 608 and 610, central controller 102 may rearrange which one or more micro particles 104 may stimulate and which one or more micro particles 104 may sense. In some embodiments, central controller 102 may instruct just a single micro particle 104 to stimulate in order to isolate the response of that stimulation and then central controller 102 may sequentially cycle through the other stimulating micro particles 104 in order to identify the response from the isolated stimulations.

System 100 as described herein may in a further illustrative embodiment be utilized in a variety of methods for treating conditions related to metabolic disorders by providing sympathetic and/or parasympathetic neuronal stimulation to provide a metabolic response in anticipation of eating. Various methods of utilizing system 100 for treating metabolic disorders and endocrine disorders will now be explained.

Figure 7:
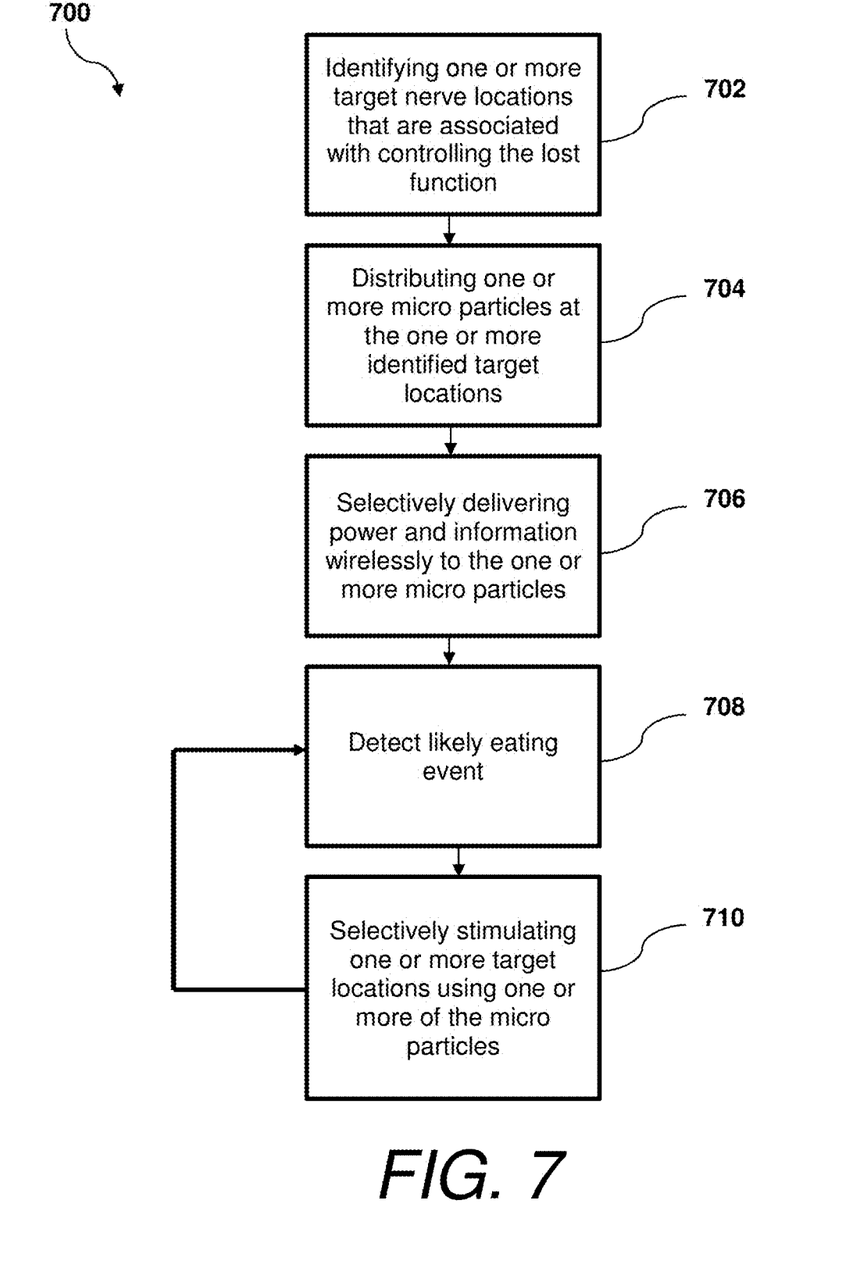
FIG. 7 is a flow chart illustrating another method of coordinated neuro stimulation, according to an exemplary embodiment.

According to an exemplary embodiment illustrated in FIG. 7, system 100 may be utilized for a method 700 of stimulating the sympathetic or parasympathetic functions of one or more organs, for instance the pancreas, of a person. Method 700 may be used for treating a person (e.g., a patient) who has diabetes, prediabetes, metabolic syndrome, or other indications that are diagnosed as related to blood sugar, such as depression, mood swings, irritability, hyperactivity, anxiety, panic attacks, mineral deficiencies, adrenal gland depletion, weight gain, hypoglycemia, candida overgrowth, hypercholesterolemia, nutrition disorders and/or chronic fatigue.

As shown in FIG. 7, method 700 may include identifying one or more target locations of one or more nerve cells that are associated with controlling the lost function, at step 702. The scope of what constitutes a target location may vary. For example, a target location may be a specific nerve cell, a specific portion of a nerve cell (e.g., dendrite, axon, axon terminal, myelin sheath, or synapse), a cluster of nerve cells, a ganglion, a nerve plexus, or a region of tissue containing one or more nerve cells. In some embodiments, target locations may be adjacent or proximate to one another, for example, two adjacent nerve cells or an axon and axon terminal of the same nerve cell. In some embodiments, target locations may be a distance apart. In some embodiments, the distance apartment may be, for example, less than, about 5 millimeters, about 10 millimeters, about 15 millimeters, about 20 millimeters, about 25 millimeters, or about 50 millimeters. In some embodiments, the distance apartment may be, for example, greater than, about 5 millimeters, about 10 millimeters, about 15 millimeters, about 20 millimeters, about 25 millimeters, or about 50 millimeters. In an illustrative embodiment, the location is proximate the celiac ganglion. In an illustrative embodiment, the location is proximate an autonomic ganglion. In a further illustrative embodiment, the location is proximate the pancreatic plexus.

Next, step 704 of method 700 may include distributing one or more micro particles into the patient (e.g., the tissue) at one or more of the identified target locations. In some embodiments, distributing the one or more micro particles 104 may include placement of one or more individual micro particles at or in the vicinity of one or more target locations. In some embodiments, distributing the one or more micro particles 104 to a target location may include directing them to a target location (e.g., a region) and within the region the one or more micro particles 104 may be more randomly distributed within the region. In some embodiments, distributing or placement of the micro particles 104 may be aided by imaging guidance. For example, a magnetic resonance (MR) imaging system may be used to provide real-time visual feedback during the distribution or placement of the micro particles.

In illustrative embodiments, the target locations can include different types of nerves, for example, motor nerves, sensory nerves, or autonomic nerves. In an illustrative embodiment, the target location is the vagus nerve.

In some embodiments, prior to distribution of the one or more micro particles, method 700 may include initiating a startup of system 100, which may include powering up of the micro particles and testing the wireless communication between central controller 102 and the micro particles 104. In some embodiments, powering up of the micro particles and testing of the wireless communication (i.e., startup) may be conducted after distribution of the one or more micro particles. In some embodiments, startup may be conducted for each micro particle after distribution of each micro particle.

Once the one or more micro particles are distributed and in position, step 706 of method 700 may include selectively delivering power and information wirelessly to one or more micro particles 104. As described herein, each individual micro particle 104 may be uniquely addressed. Thus each central controller 102 may transmit unique information to each micro particle 104.

In some embodiments, method 700 may also include selectively sensing nerve pulses at one or more target locations by one or more of the micro particles, at step 708. Central controller 102 may select which of the micro particles 104 sense nerve pulses and which stimulate nerve pulses. In some embodiments, central controller 102 may selectively instruct one or more micro particles 104 to switch from stimulating to sensing based on a stimulation protocol. In some embodiments, a micro particle 104 may stimulate and sense, for example, by using one electrode 226 to sense and another electrode 226 to stimulate. The nerve pulses may be sensed by one or more of the micro particles 104 and informational signals indicative of the sensed nerve pulse may be transmitted back to the central controller 102.

In an exemplary embodiment, the likelihood of a patient eating is monitored at step 708, and the result of this measurement used as a feedforward datum for the process 700. As discussed above, the anticipation of eating is accompanied by autonomic responses even before blood glucose levels change. A small spike in insulin production prior to consumption of a meal when a healthy person sees food or when they expect to eat. In patients with diabetics or deficient metabolic systems, this spike may not occur. Advantageously, the system and methods according to an illustrative embodiment of the present disclosure can stimulate this small insulin spike. To replace this function the stimulator can take input from user-controlled sensors or environmental device (e.g. Google Glass or other imaging device programmed for shape recognition), or other patient sensor such as an EEG monitor programmed to recognize anticipation of eating or an in-mouth sensor to detect salivary anticipation, or a voluntary user input at a time before eating.

Step 710 of method 700 may include central controller 102 selectively stimulating one or more target locations by one or more of the micro particles 104. Stimulation by the one or more micro particles 104 may trigger and action potential at the target locations, which may propagate down the nerve and on to other interconnected nerves. Central controller 102 may execute a stimulation protocol configured to conduct a coordinated stimulation by one or more of the micro particles 104 at one or more of the target locations. The stimulation protocol may be configured to stimulate (e.g., restore) a function of a limb, an organ, or other body part of a patient. The stimulations by the one or more micro particles 104 may be coordinated, for example, the stimulations may be simultaneous, the stimulations may be sequenced, or the stimulations may be patterned. In some embodiments, the stimulations may be configured to cascade, for example, central controller 102 may instruct a first micro particle 104 to stimulate a first target location and then instruct a second micro particle 104 to stimulate a second target location and then instruct a third micro particle 104 to stimulate a third target location and so on.

Steps 708 and 710 may be repeated and in between steps the stimulation and/or sensing protocol may be adjusted in order to achieve a desired result (e.g., the desired blood- or body glucose level) acting as a feedback loop. In some embodiments, method 700 may include selectively adjusting (e.g., increasing or decreasing) the power of one or more micro particle stimulations based on the sensed nerve pulses (e.g., the timing of the sensed nerve pulses). In some embodiments, between repeating of steps 708 and 710 central controller 102 may rearrange which one or more micro particles 104 may stimulate and which one or more micro particles 104 may sense. In some embodiments, central controller 102 may instruct just a single micro particle 104 to stimulate in order to isolate the response of that stimulation and then central controller 102 may sequentially cycle through the other stimulating micro particles 104 in order to identify the response from the isolated stimulations.

In addition to reassigning the task of each micro particle, in some embodiments, the characteristics of the electrical pulse used for stimulation may be adjusted. For example, the strength (e.g., voltage and/or current), amplitude, speed, duration, waveform, and frequency of the electrical pulse may be adjusted and the response to the adjustment may be sensed by one or more micro particles 104.

Although the present disclosure describes the use of system 100 and the corresponding methods primarily in reference to human patients, it is understood that system 100 and the corresponding methods may employed with mammals as well. In addition, although discussed in reference to particles, various aspects of the present disclosure can be implemented using a multicontact cuff, microelectrode array, or other suitable implantable stimulator for targeted stimulation. Various arrangements can be employed for powering a cuff, array, or other stimulator, such as a wireless battery charger for wirelessly transferring energy from outside the body, or through wires from an implanted battery-operated pulse generator.

While embodiments of the present disclosure have been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

The invention claimed is:

1. A method of stimulating an endocrine function of an organ of a patient by neuro stimulation, the method comprising:
   identifying a plurality of innervated nerves on the organ of the patient;
   defining a plurality of target locations at the plurality of innervated nerves on the organ of the patient, each target location to receive placement of at least one micro particle of a plurality of micro particles, each micro particle comprising:
      a power system that receives a wireless energy transmission; and
      an electrode system comprising a plurality of electrodes, at least one electrode to transmit an electrical pulse to the target location;
   placing each micro particle of the plurality of micro particles at a target location of the plurality of target locations;
   configuring a central controller to selectively deliver power and signals wirelessly to the plurality of micro particles, the central controller comprising:
      a power system to wirelessly deliver power to the plurality of micro particles;
      a communication system to wirelessly communicate with the plurality of micro particles; and
      a processing system to control the power system and the communication system; and
   configuring at least one of the central controller or the plurality of micro particles to selectively stimulate the endocrine function of the organ by transmitting electrical pulses to the plurality of target locations using the respective electrode of each micro particle.

2. The method of claim 1, further comprising configuring at least one of the central controller or the plurality of micro particles to selectively sense electrical pulses at the plurality of innervated nerve locations using the plurality of micro particles.

3. The method of claim 1, further comprising configuring at least one of the central controller or the plurality of micro particles to execute a stimulation protocol that stimulates the plurality of innervated nerves and senses electrical pulses at the plurality of innervated nerves.

4. The method of claim 1, wherein the organ is at least one of the pancreas, the liver, or the small intestine.

5. The method of claim 1, wherein:
   the endocrine function is a glucose level of the patient; and
   the method further comprises configuring at least one of the central controller or the plurality of micro particles to monitor the glucose level of the patient as a feedback datum.

6. The method of claim 5, wherein monitoring the glucose level comprises continuously monitoring the glucose level of the patient.

7. The method of claim 1, wherein the organ is a pancreas, and the plurality of innervated nerve locations is a plurality of islets on the pancreas.

8. A method of stimulating an endocrine function of a mammal by neuro stimulation, the method comprising:
identifying a plurality of innervated nerves on an organ of the mammal associated with the control of the endocrine function to be stimulated by a plurality of stimulators, each stimulator comprising:
a power system to receive a wireless energy transmission; and
a plurality of microelectrodes;
defining a plurality of target locations at the plurality of innervated nerves on the organ of the mammal, each target location to receive placement of a stimulator of the plurality of stimulators;
placing each stimulator of the plurality of stimulators at a target location of the plurality of target locations on the organ of the mammal; and
configuring a central controller to selectively deliver power and signals wirelessly to each stimulator of the plurality of stimulators to selectively stimulate the plurality of innervated nerves, the central controller comprising:
a power system to wirelessly deliver power to the plurality of microelectrodes;
a communication system to wirelessly communicate with the stimulator; and
a processing system to control the power system and the communication system.

9. The method of claim 8, further comprising configuring at least one of the central controller or the plurality of stimulators to selectively sense electrical pulses at the plurality of innervated nerves using stimulator.

10. The method of claim 8, further comprising configuring at least one of the central controller or the plurality of stimulators to execute a stimulation protocol that stimulates the plurality of innervated nerves and senses electrical pulses at the plurality of innervated nerves.

11. The method of claim 8, wherein the organ is at least one of the pancreas, the liver, or the small intestine.

12. The method of claim 8, wherein
the endocrine function is a glucose level of the mammal.

13. The method of claim 8, wherein selectively stimulating the plurality of innervated nerves stimulates beta cells of the organ.

14. The method of claim 8, wherein the organ is a pancreas, and the plurality of innervated nerves is a plurality of islets on the pancreas.

15. A method for neuro stimulation, comprising:
identifying a plurality of islets on a pancreas of a human subject;
defining a plurality of target locations at the plurality of islets, each target location to receive placement of at least one micro particle of a plurality of micro particles, each micro particle of the plurality of micro particles comprising:
a power system to receive wireless energy transmissions; and
an electrode system comprising a plurality of electrodes, at least one electrode to transmit an electrical pulse for stimulating a corresponding islet of the plurality of islets on the pancreas of the human subject; and
initiating a startup of each micro particle and a central controller, the central controller to control the plurality of micro particles, and comprising:
a power system to wirelessly deliver power to the plurality of micro particles;
a communication system to wirelessly communicate with the plurality of micro particles; and
a processing system to control the power system and the communication system; and
placing each micro particle of the plurality of micro particles at a target location of the plurality of target locations.

16. The method of claim 15, wherein each islet of the plurality of islets is disposed on a different side of the pancreas.

17. The method of claim 15, wherein initiating the startup of each micro particle and the central controller comprises:
powering up each micro particle of the plurality of micro particles; and
testing wireless communications between each of the plurality of micro particles and the central controller.

18. The method of claim 15, wherein initiating the startup of each micro particle and the central controller is performed prior to placing each micro particle of the plurality of micro particles at the target location of the plurality of target locations.

19. The method of claim 15, wherein initiating the startup of each micro particle and the central controller is performed after placing each micro particle of the plurality of micro particles at the target location of the plurality of target locations.

20. The method of claim 15, wherein the central controller is configured to execute a stimulation protocol comprising a coordinated stimulation by each micro particle of the plurality of micro particles at the plurality of target locations.

21. The method of claim 15, wherein placing each micro particle of the plurality of micro particles comprises using a magnetic resonance (MR) imaging system to provide real-time feedback.

22. The method of claim 15, wherein each micro particle is configured to stimulate and sense electrical pulses at each islet.

23. The method of claim 22, wherein each micro particle is configured to wirelessly transmit informational signals to the central controller indicative of the electrical pulses sensed at the respective islet.

24. The method of claim 22, wherein the plurality of micro particles are each uniquely addressable to enable the central controller to communicate with each micro particle individually.

25. The method of claim 22, wherein the central controller is configured to individually instruct each micro particle to cascade electrical pulses.

26. The method of claim 15, wherein each micro particle has an average diameter of less than 500 micrometers.

27. The method of claim 15, wherein the central controller is configured to instruct each micro particle to transmit one or more electrical pulses to the plurality of islets to stimulate beta cells of the pancreas.

28. The method of claim 15, further comprising identifying a plurality of axons of the corresponding plurality of islets, and wherein defining the plurality of target locations comprises defining the plurality of target locations at the plurality of axons.

29. The method of claim 15, further comprising identifying a plurality of axon terminals of the corresponding plurality of islets, and wherein defining the plurality of target locations comprises defining the plurality of target locations at the plurality of axon terminals.

30. The method of claim 15, further comprising identifying a plurality of dendrites of the corresponding plurality of islets, and wherein defining the plurality of target locations comprises defining the plurality of target locations at the plurality of dendrites.

31. The method of claim 15, further comprising identifying a plurality of synapses of the corresponding plurality of islets, and wherein defining the plurality of target locations comprises defining the plurality of target locations at the plurality of synapses.

\* \* \* \* \*